United States Patent
Gliner (10) Patent No.: US 12,427,060 B2
(45) Date of Patent: Sep. 30, 2025

(54) PHACOEMULSIFICATION PROBE STROKE LENGTH MAXIMIZATION SYSTEM

(71) Applicant: JOHNSON & JOHNSON SURGICAL VISION, INC., Irvine, CA (US)

(72) Inventor: Vadim Gliner, Haifa (IL)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 0 days.

(21) Appl. No.: 18/390,693

(22) Filed: Dec. 20, 2023

(65) Prior Publication Data

US 2024/0115422 A1 Apr. 11, 2024

Related U.S. Application Data

(62) Division of application No. 17/087,665, filed on Nov. 3, 2020, now Pat. No. 11,883,326.

(51) Int. Cl.
*A61F 9/007* (2006.01)
*A61B 17/00* (2006.01)
*A61B 90/00* (2016.01)

(52) U.S. Cl.
CPC .......... *A61F 9/00745* (2013.01); *A61B 90/06* (2016.02); *A61B 2017/00402* (2013.01); *A61B 2217/007* (2013.01)

(58) Field of Classification Search
CPC ................. A61F 9/00745; A61B 90/06; A61B 2017/00402; A61B 2217/007
See application file for complete search history.

(56) References Cited

U.S. PATENT DOCUMENTS

| 4,918,492 A | 4/1990 | Ferdinand et al. |
| 5,843,109 A | 12/1998 | Mehta et al. |
| 6,175,180 B1 * | 1/2001 | Angelini ............ A61F 9/00745 310/318 |

(Continued)

FOREIGN PATENT DOCUMENTS

| EP | 0 424 685 A2 | 5/1991 |
| WO | 2020/160434 A1 | 8/2020 |

OTHER PUBLICATIONS

Y C Huang et al., A piezoelectric vibration-based syringe for reducing insertion force, 2012 IOP Conf. Ser.: Mater. Sci. Eng. 42, Jan. 2020, 5 pages.

(Continued)

*Primary Examiner* — Andrew P. Restaino (57) ABSTRACT

A phacoemulsification system including a phacoemulsification probe having a probe body, a horn disposed at least partially in the probe body, a needle coupled with the horn and configured to be inserted into an eye, and a piezoelectric actuator disposed in the probe body and configured to vibrate the horn and the needle in a first direction with a stroke length with respect to the probe body; a signal generator configured to generate a drive signal to drive a vibration of the piezoelectric actuator; a stroke measurement apparatus configured to provide indications of the stroke length of the needle over time; and a controller configured to dynamically adjust a frequency of the drive signal so as to maximize the stroke length and maintain mechanical resonance of the needle responsively to the provided indications of the stroke length.

13 Claims, 6 Drawing Sheets

(56) References Cited

U.S. PATENT DOCUMENTS

| | | |
|---|---|---|
| 6,710,880 B1 | 3/2004 | Zhao et al. |
| 6,852,092 B2 | 2/2005 | Kadziauskas et al. |
| 7,169,123 B2 | 1/2007 | Kadziauskas et al. |
| 7,554,343 B2 | 6/2009 | Bromfield |
| 7,871,420 B2 | 1/2011 | Anderson et al. |
| 9,107,730 B2 | 8/2015 | Huculak et al. |
| 9,913,752 B2 | 3/2018 | Hauger |
| 10,258,505 B2 | 4/2019 | Ovchinnikov |
| 10,596,032 B2 | 3/2020 | Raney |
| 2004/0092921 A1 | 5/2004 | Kadziauskas et al. |
| 2005/0209621 A1 | 9/2005 | Gordon et al. |
| 2009/0287092 A1 | 11/2009 | Leo et al. |
| 2010/0160852 A1 | 6/2010 | Moore |
| 2012/0071922 A1 | 3/2012 | Shanley et al. |
| 2013/0204142 A1 | 8/2013 | Bertholds et al. |
| 2013/0314077 A1 | 11/2013 | Okada et al. |
| 2016/0174834 A1* | 6/2016 | Eslami .................. A61B 8/485 351/246 |
| 2016/0302966 A1* | 10/2016 | Moradian ........... A61F 9/00745 |
| 2019/0365567 A1 | 12/2019 | Balkenbush et al. |

OTHER PUBLICATIONS

Barbosa et al., A simple interferometric method to measure the calibration factor and displacement amplification in piezoelectric flextensional actuators., Sba Controle & Automação [online]. 2010, vol. 21, n.6 [cited Nov. 2, 2020], pp. 577-587.

Wang et al., "Laser ultrasonic surface wave dispersion technique for non-destructive evaluation of human dental enamel," Opt. Express 17, 15592-15607 (2009).

PCT International Search Report for International Application No. PCT/IB2021/059880, dated Jan. 28, 2022, 7 pages.

* cited by examiner

PHACOEMULSIFICATION PROBE STROKE LENGTH MAXIMIZATION SYSTEM

CROSS-REFERENCE TO RELATED APPLICATIONS

This application is a divisional of U.S. application Ser. No. 17/087,665, filed 3 Nov. 2020, now U.S. Pat. No. 11,883,326, granted 30 Jan. 2024, which is hereby incorporated by reference in its entirety.

FIELD OF THE INVENTION

The present invention relates to medical systems, and in particular, but not exclusively to, phacoemulsification.

BACKGROUND

A cataract is a clouding and hardening of the eye's natural lens, a structure which is positioned behind the cornea, iris and pupil. The lens is mostly made up of water and protein and as people age these proteins change and may begin to clump together obscuring portions of the lens. To correct this a physician may recommend phacoemulsification cataract surgery. Before the procedure, the surgeon numbs the area with anesthesia. Then a small incision is made in the sclera or clear cornea of the eye. Fluids are injected into this incision to support the surrounding structures. The anterior surface of the lens capsule is then removed to gain access to the cataract. The surgeon then uses a phacoemulsification probe, which has an ultrasonic handpiece with a titanium or steel needle. The tip of the needle vibrates at ultrasonic frequency to sculpt and emulsify the cataract while a pump aspirates lens particles and fluid from the eye through the tip. The pump is typically controlled with a microprocessor.

The pump may be a peristaltic and/or a venturi type of pump. Aspirated fluids are replaced with irrigation of a balanced salt solution to maintain the anterior chamber of the eye. After removing the cataract with phacoemulsification, the softer outer lens cortex is removed with suction. An intraocular lens (IOL) is introduced into the empty lens capsule. Small struts called haptics hold the IOL in place. Once correctly installed the IOL restores the patient's vision.

SUMMARY

There is provided in accordance with an embodiment of the present disclosure, a phacoemulsification system, including a phacoemulsification probe including a probe body, a horn disposed at least partially in the probe body, a needle mounted in the horn and configured to be inserted into a lens capsule of an eye, and a piezoelectric actuator disposed in the probe body and configured to vibrate the horn and the needle in one or more directions, e.g. a longitudinal direction, transverse direction, and/or torsional direction, with a stroke length with respect to the probe body, a signal generator configured to generate a drive signal to drive a vibration of the piezoelectric actuator, a stroke measurement apparatus configured to provide respective indications of the stroke length of the needle over time, and a controller configured to perform respective adjustments of a frequency of the drive signal so as to maximize the stroke length and maintain mechanical resonance of the needle responsively to the provided respective indications of the stroke length.

Further in accordance with an embodiment of the present disclosure the stroke measurement apparatus includes an interferometer.

Still further in accordance with an embodiment of the present disclosure the interferometer includes a Michaelson Interferometer.

Additionally in accordance with an embodiment of the present disclosure the interferometer includes a first part and a second part, the phacoemulsification probe including a vibrating portion including the horn and the needle, the vibrating portion being configured to vibrate in the longitudinal direction with respect to the probe body, the first part of the interferometer being disposed on the vibrating portion, the second part of the interferometer being disposed on the probe body.

Moreover, in accordance with an embodiment of the present disclosure the first part of the interferometer includes a first reflector, the second part of the interferometer includes at least one optical fiber disposed on the probe body.

Further in accordance with an embodiment of the present disclosure the first reflector is disposed on the horn.

Still further in accordance with an embodiment of the present disclosure, the system includes a console including the controller, wherein the interferometer includes a third part also disposed in the console, the third part of the interferometer includes a second reflector, a beam splitter-combiner, a light source configured to generate an optical signal, and a detector; and the at least one optical fiber extends from the probe body to the beam splitter-combiner in the console.

Additionally in accordance with an embodiment of the present disclosure the beam-splitter-combiner is configured to receive the optical signal from the light source, split the received optical signal into a first part directed to the first reflector and a second part directed to the second reflector, and combine the first part reflected by the first reflector and the second part reflected by the second reflector into a combined optical signal directed to the detector.

Moreover, in accordance with an embodiment of the present disclosure the at least one optical fiber includes a first optical fiber configured to convey the first part of the optical signal from the beam-splitter-combiner to the first reflector, and a second optical fiber configured to convey the first part of the optical signal reflected by the first reflector to the beam splitter-combiner.

Further in accordance with an embodiment of the present disclosure the beam splitter-combiner includes a directional optical fiber coupler.

There is also provided in accordance with another embodiment of the present disclosure a phacoemulsification method including inserting a needle of a phacoemulsification probe into a lens capsule of an eye, generating a drive signal to drive a vibration of a piezoelectric actuator of the probe causing vibration of the needle in a longitudinal direction with a stroke length with respect to a probe body of the phacoemulsification probe, providing indications of the stroke length of the needle over time, and dynamically adjusting a frequency of the drive signal so as to maximize the stroke length and maintain mechanical resonance of the needle responsively to the provided indications of the stroke length.

Still further in accordance with an embodiment of the present disclosure, the method includes vibrating a vibrating portion of the phacoemulsification probe in the longitudinal direction with respect to the probe body, a first part of an interferometer being disposed on the vibrating portion, a second part of the interferometer being disposed on the probe body.

Additionally, in accordance with an embodiment of the present disclosure the first part of the interferometer includes a first reflector, the second part of the interferometer includes at least one optical fiber disposed on the probe body.

Moreover, in accordance with an embodiment of the present disclosure the first reflector is coupled with a horn of the vibrating portion.

Further in accordance with an embodiment of the present disclosure, the method includes receiving an optical signal from a light source, splitting the received optical signal into a first part directed to the first reflector and a second part directed to a second reflector, and combining the first part reflected by the first reflector and the second part reflected by the second reflector into a combined optical signal directed to the detector.

Still further in accordance with an embodiment of the present disclosure the at least one optical fiber includes a first optical fiber and a second optical fiber, the method further including conveying the first part of the optical signal from the beam-splitter-combiner to the first reflector in the first optical fiber, and conveying the first part of the optical signal reflected by the first reflector to the beam splitter-combiner in the second optical fiber.

Additionally, in accordance with an embodiment of the present disclosure the splitting and combining are performed by a directional optical fiber coupler.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

A phacoemulsification probe typically includes a piezoelectric actuator to drive a needle of the phacoemulsification probe during a cataract procedure. The stroke length of the needle is not only a function of the voltage applied to the piezoelectric actuator of the probe, but is generally at a maximum when the piezoelectric actuator is operating at its resonant frequency. The stroke length may be any suitable value but is generally in the range of 20-40 microns, When the piezoelectric actuator is not operating at its resonant frequency, the stroke length is less than the maximum and the electrical energy used to power the piezoelectric actuator is converted to heat thereby heating the phacoemulsification probe.

The resonant frequency may depend on the geometry of the rest of the probe and other factors such as temperature of the piezoelectric actuator, the voltage and current amplitude applied to the piezoelectric actuator, and acoustic impedance encountered by the piezoelectric actuator. For example, the resonant frequency of the piezoelectric actuator may change when a load is applied to the needle. Therefore, when the needle is outside the eye, the resonant frequency is at one value, and when the needle is inserted into the eye, the resonant frequency changes to another value, and when the needle is impacting a cataract, the resonant frequency changes to yet another value.

As previously mentioned, another factor that affects the resonant frequency of the piezoelectric actuator is temperature. So, for example, if the resonant frequency of the piezoelectric actuator changes due to the needle impacting a cataract, and the piezoelectric actuator is still powered with the same frequency signal, the piezoelectric actuator will start to heat and the stoke length will decrease. The additional heat will lead to further changes in the resonant frequency, which in turn leads to further heat and reduced stroke length, and so on.

The resonant frequency of the piezoelectric actuator is non-linear and inadequate control can lead to the phacoemulsification probe providing an inadequate needle stroke length and becoming too hot for the eye. For example, the phacoemulsification probe could reach a temperature of 42 degrees Celsius, above which the proteins in the eye could coagulate, which is very dangerous for the eye.

Therefore, irrigation is used to reduce the temperature of the phacoemulsification probe. However, irrigation has its own problems as irrigation without carefully matched aspiration can lead to too much pressure in the eye, which is dangerous, whereas too much aspiration can lead to the eye collapsing. Moreover, irrigation may not be sufficient to adequately cool the phacoemulsification probe.

Embodiments of the present invention solve the above problems by providing a phacoemulsification system that dynamically adjusts a frequency of a drive signal driving a piezoelectric actuator of a phacoemulsification probe to follow the mechanical resonance of the probe (e.g., the mechanical resonance of the piezoelectric actuator, horn, and needle of the probe) responsively to indications of stroke length of the probe needle over time thereby maximizing stroke length while minimizing temperature rise of the phacoemulsification probe.

The stroke length may be measured by any suitable apparatus, such as an interferometer, e.g., a Michaelson Interferometer. The interferometer may include any suitable components. In some embodiments, the interferometer includes a light source, a detector, a beam splitter-combiner and two reflectors (e.g., mirrors). In some embodiments, part of the interferometer is included in the probe and part of the interferometer is included in a console. The different parts of the interferometer may be connected by one or more optical fibers.

In some embodiments, a reflector (e.g., mirror) is connected to a part of the probe which vibrates, e.g., the horn or needle of the probe. One or more optical fibers are then connected to an element of the probe which does not vibrate, such as the probe body. The optical fibers extend from the probe body to the beam-splitter-combiner, which is included in the part of the interferometer included in the console. The part of the interferometer included in the console may also include the light source, another reflector, and the detector. The interferometer then provides a measure of the distance between the end(s) of the optical fiber(s) connected to the probe body and the reflector and therefore provides an indication of the needle stroke length. In some embodiments, the distribution of elements of the interferometer between the probe and the console may differ. In some embodiments, all of the elements of the interferometer may be disposed in the probe.

The system includes a controller (e.g., a micro controller, an application specific controller, or controlling circuitry), which adjusts the frequency of the drive signal to maximize the stroke length and maintain mechanical resonance of the needle responsively to indications of the stroke length provided by the interferometer. The frequency may be adjusted using any suitable method, for example, using an optimization algorithm, for example, but not limited to, a gradient descent algorithm. The output of the detector of the interferometer may be digital or analog. If the output of the detector is in analog form, the output may be converted to digital form for processing by the controller. In some embodiments, the controller may adjust the drive signal frequency to maximize the stroke length using analog processing circuits.

System Description

Figure 1:
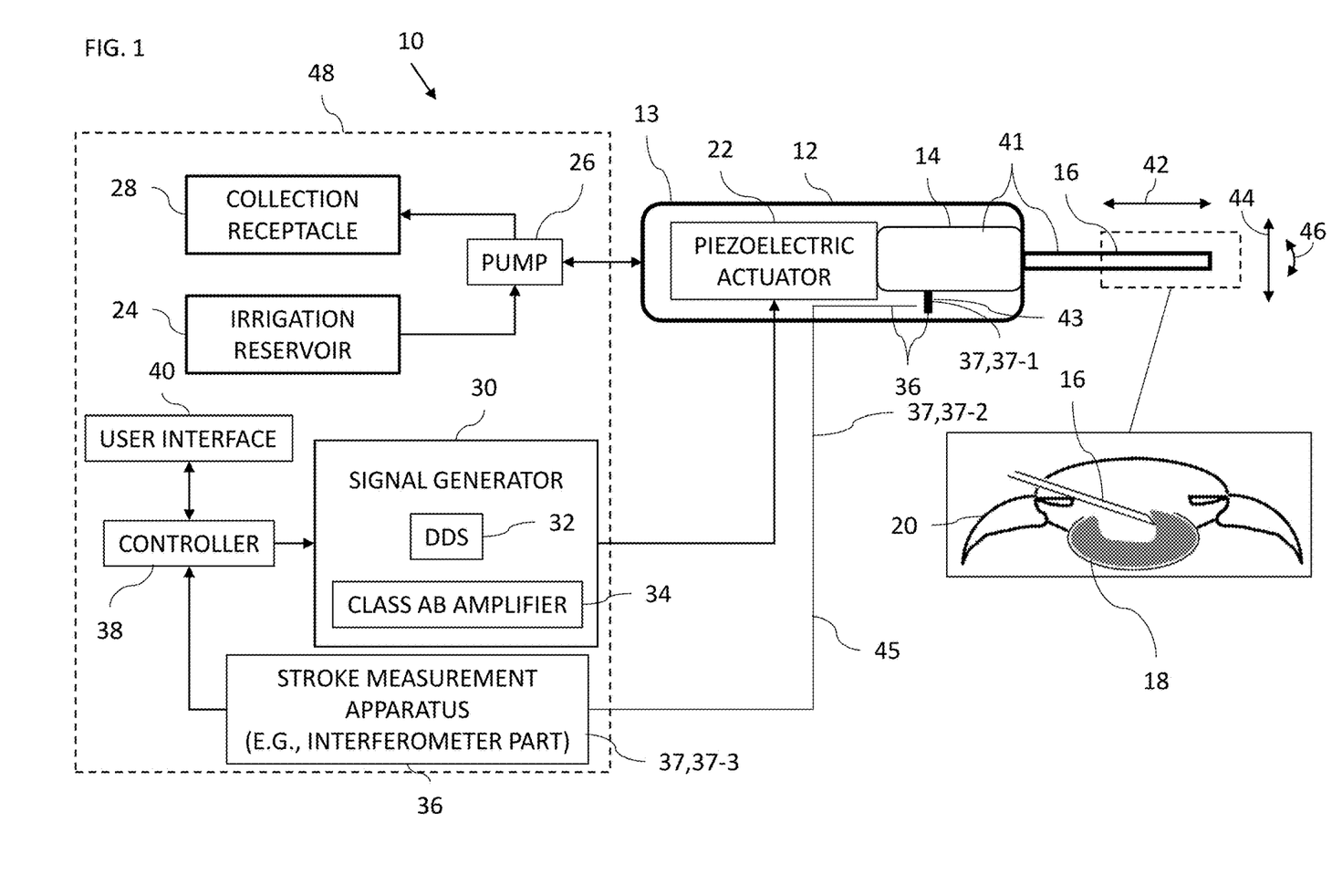
FIG. 1 is a partly pictorial, partly block diagram view of a phacoemulsification system constructed and operative in accordance with an embodiment of the present invention.
Figure 2:
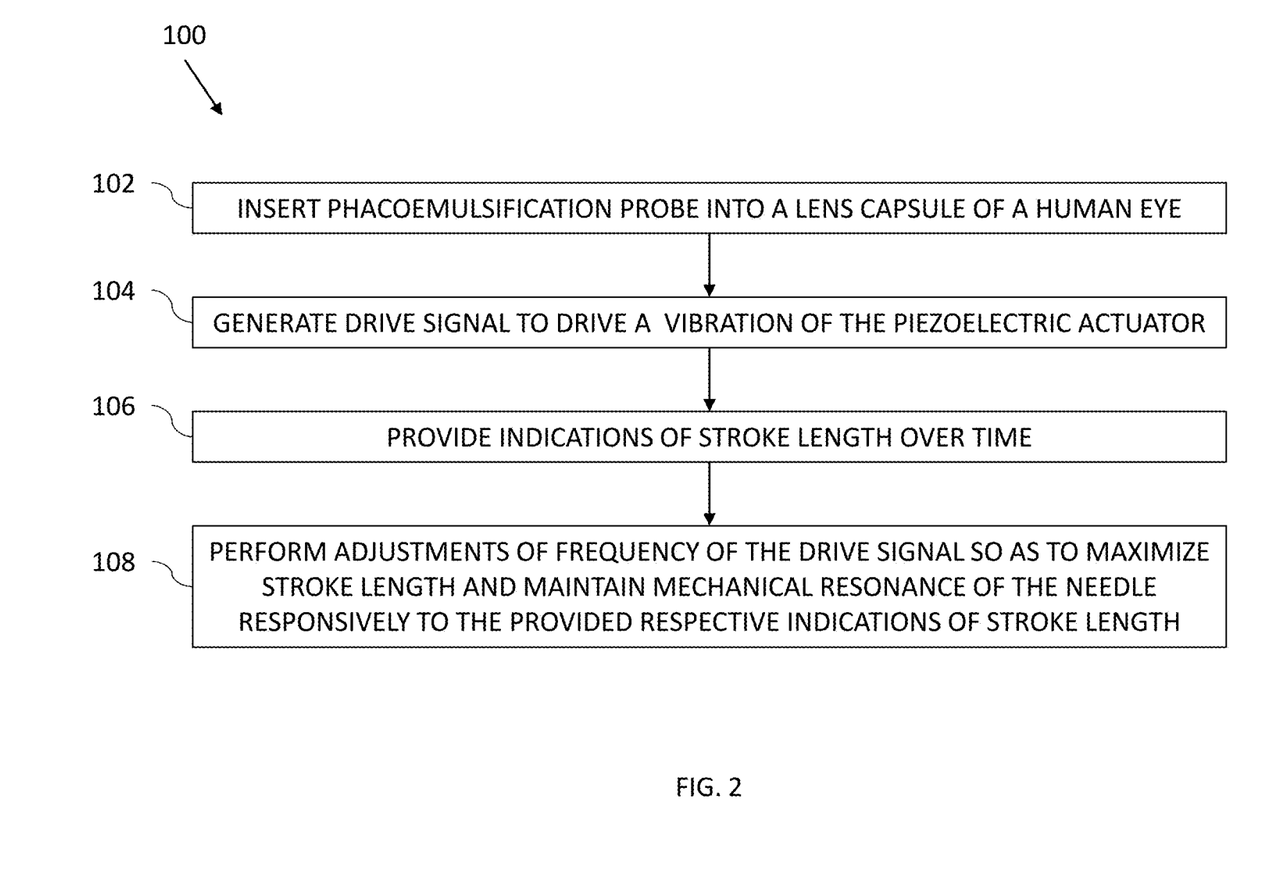
FIG. 2 is a flowchart including steps in a method of operation of the system of FIG. 1.

Reference is now made to FIG. 1, which is a partly pictorial, partly block diagram view of a phacoemulsification system 10 constructed and operative in accordance with an embodiment of the present invention. Reference is also made to FIG. 2, which is a flowchart 100 including steps in a method of operation of the system 10 of FIG. 1.

The phacoemulsification system 10 includes a phacoemulsification probe 12 including a probe body 13, a horn 14 at least partially disposed in the probe body 13, a needle 16 coupled with the horn 14 and configured to be inserted (block 102 of FIG. 2) into a lens capsule 18 of an eye 20, and a piezoelectric actuator 22 disposed in the probe body 13 and configured to vibrate the horn 14 and the needle 16 in a one or more directions (e.g. longitudinal, transverse, or a combination thereof) with a stroke length with respect to the probe body 13. The longitudinal direction is defined as a direction parallel to an axis (e.g., directional of elongation) of the needle 16. The horn 14 and needle 16 vibrate with respect to the probe body 13, which is generally non-vibrating. The vibration of the needle 16 is used to break the cataract into small pieces during the phacoemulsification procedure.

The term "stroke length with respect to the probe body", as used in the specification and claims, is defined as the maximum movement of the needle 16 with respect to the probe body 13 during vibration of the horn 14 and the needle 16, and is dependent on the mode of vibration of the horn 14 and needle 16. For example, if the needle 16 is vibrating is a direction parallel to a longitudinal axis of the probe 12, the stroke length is measured parallel to the longitudinal axis.

The phacoemulsification probe 12 is connected to an irrigation reservoir 24 via a pumping sub-system 26 and to a collection receptacle 28 via the pumping sub-system 26. Irrigation fluid is pumped from the irrigation reservoir 24 by the pumping sub-system 26 to a distal end of the phacoemulsification probe 12 for irrigating the eye during the phacoemulsification procedure. Waste matter (e.g., emulsified parts of the cataract) and eye fluid are aspirated via the needle 16 to the collection receptacle 28 using the pumping sub-system 26. The pumping sub-system 26 may comprise one or more pumps of any suitable pump type, such as peristaltic pumps, vane pumps, or any suitable combination thereof. In an embodiment, the irrigation fluid may be administered to phacoemulsification probe 12 via a gravity fed and/or pressurized bottle/bag. The phacoemulsification probe 12 is described in more detail with reference to FIG. 3.

The phacoemulsification system 10 includes a signal generator 30, which is coupled with the piezoelectric actuator 22, and is configured to generate a drive signal to drive a vibration of the piezoelectric actuator 22 (block 104 of FIG. 2). In some embodiments, the signal generator 30 includes a direct digital synthesizer (DDS) 32 and an amplifier 34 (e.g. class AB, class D, etc.), which are coupled together. The amplifier 34 is coupled with the piezoelectric actuator 22. The DDS 32 is configured to generate the drive signal. The amplifier 34 is configured to amplify the drive signal to power the piezoelectric actuator 22. The DDS 32 may be replaced by any suitable signal synthesizer. The amplifier 34 may be any suitable signal amplifier, for example, but not limited to a class D amplifier.

The phacoemulsification system 10 includes a stroke measurement apparatus 36 and a controller 38. The stroke measurement apparatus 36 is configured to provide to the controller 38 respective indications of the stroke length of the needle 16 over time (block 106 of FIG. 2) in one or more of the directions in which the needle is vibrating. In some embodiments, the stroke measurement apparatus 36 includes an interferometer 37. In some embodiments, the interferometer 37 includes a Michaelson Interferometer or a fiber optic Fabry Perot interferometer, by way of example.

The phacoemulsification probe 12 includes a vibrating portion 41 comprising the horn 14 and the needle 16. The vibrating portion 41 is configured to vibrate in a direction with respect to the probe body 13. The vibration direction may include any one or more of the following: a longitudinal direction; a transverse direction; a torsional direction, or any suitable combination thereof. The interferometer 37 may include several parts 37-1, 37-2, 37-3. Part 37-1 of the interferometer 37 is coupled with (or disposed on) the vibrating portion 41, part 37-2 of the interferometer 37 is coupled with the probe body 13, and part 37-3 of the interferometer 37 is typically coupled with or disposed in a console 48. In some embodiments, part 37-1 of the interferometer 37 may include a reflector 43 coupled with the vibrating portion 41, and part 37-2 of the interferometer may include at least one optical fiber 45 coupled with the probe body 13 and extends to the part 37-3 of the interferometer 37 coupled with or disposed in the console 48. In some embodiments, the reflector 43 is coupled with the horn 14. The interferometer is described in more detail with reference to FIG. 4.

In some embodiments, the stroke measurement apparatus 36 may include multiple interferometers 37 measuring the movement of the vibrating portion 41 in different directions so as to provide a measure of the stroke of the needle 16 whether the needle 16 is vibrating in a longitudinal direction, a transverse direction, a torsional direction, or any suitable combination thereof as described in more detail with reference to FIG. 6.

The console 48 may also house one or more of the following: the irrigation reservoir 24, pumping sub-system 26, collection receptacle 28, signal generator 30, stroke measurement apparatus 36, controller 38, and/or a user interface 40.

The controller 38 may be replaced by any suitable controller or processor to perform the functions of the controller 38 as described herein. In practice, some or all of the functions of the controller 38 may be combined in a single physical component or, alternatively, implemented using multiple physical components. These physical components may comprise hard-wired or programmable devices, or a combination of the two. In some embodiments, at least some of the functions of the controller 38 may be carried out by a programmable processor under the control of suitable software. This software may be downloaded to a device in electronic form, over a network, for example. Alternatively, or additionally, the software may be stored in tangible, non-transitory computer-readable storage media, such as optical, magnetic, or electronic memory.

The controller 38 may receive user-based commands via the user interface 40, which may include setting a vibration mode and/or frequency of the piezoelectric actuator 22, adjusting the vibration mode and/or frequency of the piezoelectric actuator 22, setting or adjusting a stroke amplitude of the needle 16, and/or setting or adjusting an irrigation and/or aspiration rate of the pumping sub-system 26. The controller 38 is configured to control the pumping sub-system 26 and the signal generator 30 based on the user-based commands. The user interface 40 may include any suitable user interface devices, for example, but not limited to any one or more of the following: a keyboard, a keypad, a touch screen, a pointing device (such as a mouse, stylus, or joystick), a remote, or a footpedal.

The controller 38 is configured to perform respective adjustments of a frequency of the drive signal (generated by the signal generator 30) so as to maximize the stroke length and maintain mechanical resonance of the needle 16 responsively to the provided respective indications of the stroke length (block 108 of FIG. 2). It should be noted that the term "mechanical resonance of the needle", in all grammatical forms thereof, is defined as approximately vibrating at the mechanical resonance, due to noise, thermal effects and bandwidth limitations, for example. The controller 38 may adjust the frequency of the drive signal to maximize the stroke length using any suitable method, for example, based on an optimization algorithm, for example, but not limited to, including a gradient descent algorithm. An example optimization method for use in the phacoemulsification system 10 is described with reference to FIG. 5.

In some embodiments the piezoelectric actuator 22 may include a single resonance mode, for example, a longitudinal resonance mode (indicated using arrow 42), or a transverse resonance mode (indicated using arrow 44), or a torsional resonance mode (indicated using arrow 46). In some embodiments, the piezoelectric actuator 22 may include two (or more) different resonance modes having two (or more) respective resonant frequencies. The resonance modes may include any suitable resonance modes, for example, any two or more of the following: the longitudinal resonance mode (indicated using arrow 42), or the transverse resonance mode (indicated using arrow 44), or the torsional resonance mode (indicated using arrow 46).

The needle 16 shown in FIG. 1 is a straight needle. Any suitable needle may be used with the phacoemulsification probe 12, for example, a curved or bent tip needle commercially available from Johnson & Johnson Surgical Vision, Inc., Santa Ana, CA, USA.

Figure 3:
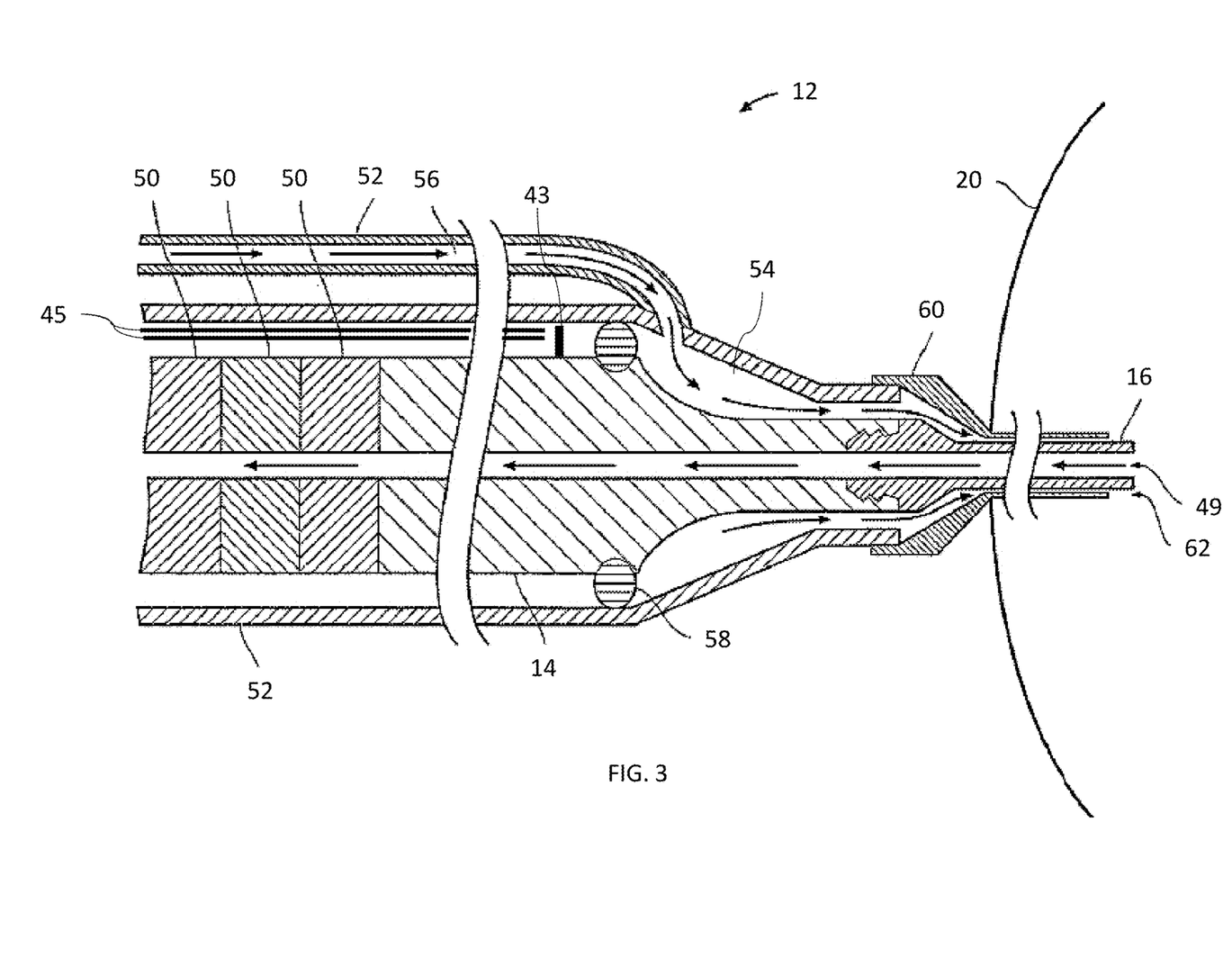
FIG. 3 is a schematic view of a phacoemulsification probe for use in the system of FIG. 1.

Reference is now made to FIG. 3, which is a schematic view of the phacoemulsification probe 12 for use in the system 10 of FIG. 1. Generally, the phacoemulsification probe 12 includes the needle 16, defining a lumen that is operatively coupled to the collection receptacle 28 (FIG. 1) via the pumping sub-system 26 (FIG. 1) forming an aspiration line 49. The proximal end of the needle 16 is coupled with horn 14, which has its proximal end coupled with a set of piezoelectric crystals 50 of the piezoelectric actuator 22 (FIG. 1), shown as three rings. The horn 14, crystals 50, and a proximal portion of the needle 16 are enclosed within a handpiece casing 52 (comprised in the probe body 13 (FIG. 1)) having an irrigation port coupled to an irrigation line 54 defining an irrigation pathway 56. The irrigation line 54 is coupled with irrigation reservoir 24 (FIG. 1). The horn 14 is typically an integrated metal structure, formed from any suitable metal, such as titanium, and often includes a rubber O ring 58 around the mid-section, just before the horn 14 tapers to fit with the needle 16 at the distal end of horn 14. The O ring 58 snugly fits between the horn 14 and the casing 52. The O ring 58 seals the proximal portion of the horn 14 from the irrigation pathway 56. Thus, there is a channel of air defined between the horn 14 and the casing 52. Descriptions of handpieces known in the art are provided in U.S. Pat. No. 6,852,092 to Kadziauskas, et al., and U.S. Pat. No. 5,843,109 to Mehta, et al., by way of example.

The embodiment of the phacoemulsification probe 12 described with reference to FIG. 3 is described by way of example only. Any suitable phacoemulsification probe may be used instead of the phacoemulsification probe 12.

In preparation for the phacoemulsification procedure, a sleeve 60 is typically added to the distal end of the phacoemulsification probe 12, covering a portion of the needle 16 (thus, exposing the distal tip of the needle 16), and the distal end of the irrigation pathway 56, thereby extending the pathway 56 and defining an irrigation port 62 just before the distal tip of the needle 16. In an embodiment, one or more irrigation ports 62 may be located in a wall of the distal end of sleeve 60. The needle 16 and a portion of the sleeve 60 are then inserted through the cornea of the eye 20 to reach the lens capsule 18 (FIG. 1).

During the phacoemulsification procedure, the irrigation pathway 56, the anterior chamber of the eye and the aspiration line 49 form a fluidic circuit, where irrigation fluid enters the anterior chamber via the irrigation pathway 56 and port 62, and is then aspirated through the aspiration line 49 along with other materials that the surgeon desires to aspirate out, such as the cataract. If, however, the materials, such as the cataract, are too hard and/or large to be aspirated through the aspiration line 49, the distal end of the needle 16 is ultrasonically vibrated to emulsify the material into a size and state that can be successfully aspirated.

The needle 16 is ultrasonically vibrated by applying electric power to the piezoelectric crystals 50, which in turn, cause the horn 14 to ultrasonically vibrate, which in turn, ultrasonically vibrates the needle 16. The electric power is defined by a number of parameters, such as signal frequency and amplitude, and if the power is applied in pulses, then the parameters can further include pulse width, shape, size, duty cycle, amplitude, and so on. These parameters are controlled by the controller 38 (FIG. 1) and example control of these parameters is described in U.S. Pat. No. 7,169,123 to Kadziauskas, et al.

FIG. 3 also shows the reflector 43 of the interferometer 37 (FIG. 1) coupled with the horn 14, and the optical fiber(s) 45 of the interferometer 37 coupled with the handpiece casing 52 of the probe body 13 (FIG. 1).

Figure 4:
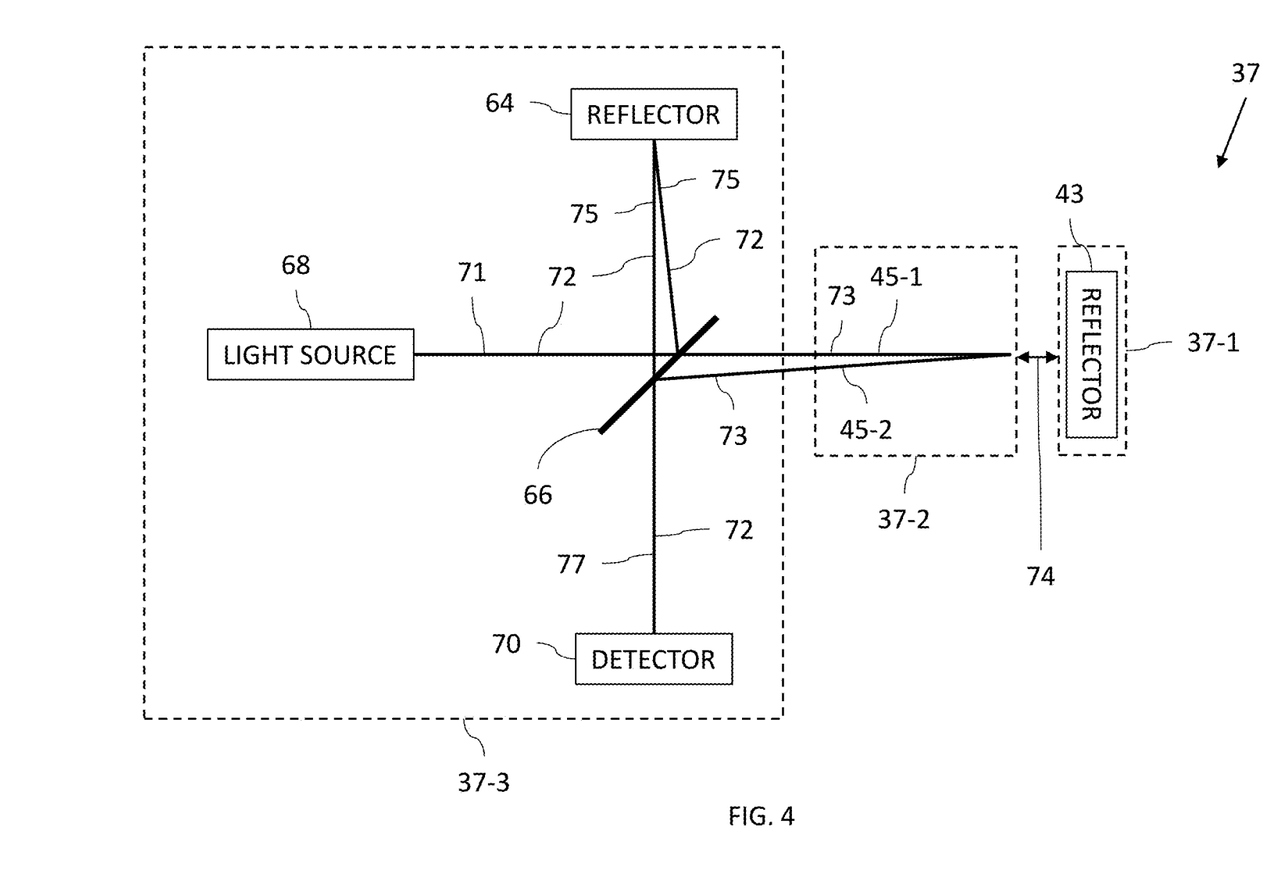
FIG. 4 is a schematic view of an interferometer for use in the system of FIG. 1.

Reference is now made to FIG. 4, which is a schematic view of the interferometer 37 for use in the system 10 of FIG. 1. As previously mentioned, the interferometer 37 comprises three parts 37-1, 37-2, and 37-3. Part 37-1 includes the reflector 43 coupled with the vibrating portion 41 (FIG. 1), part 37-2 includes the optical fiber(s) 45 (45-1 and 45-2), and part 37-3 is coupled with or disposed in the console 48 (FIG. 1) and includes a reflector 64 (e.g., a mirror), a beam splitter-combiner 66, a light source 68 configured to generate an optical signal 71, and a detector 70. The optical fiber(s) 45 extend(s) from the probe body 13 (FIG. 1) to the beam splitter-combiner 66, which is disposed in the console 48 (FIG. 1).

The beam splitter-combiner 66 is configured to: receive the optical signal 71 from the light source 68; split the received optical signal 71 into a first part 73 directed to the reflector 43, and a second part 75 directed to the reflector 64; and combine the first part 73 of the optical signal 71 reflected by the reflector 43 and the second part 75 of the optical signal 71 reflected by the reflector 64 into a combined optical signal 77 directed to the detector 70.

The detector 70 is configured to detect the combined optical signal 77 received from the beam splitter-combiner 66. The combined optical signal 77 exhibits an interference pattern which is a function of a distance 74 between the end(s) of the optical fiber(s) 45 and the reflector 43. In some embodiments, the detector 70 detects the spacing of the interference pattern and outputs a signal to the controller 38 (FIG. 1) responsively to the detected spacing. Therefore, the signal output by the detector 70 to the controller 38 is an indication of the distance 74 and also the stroke length of the needle 16 (FIG. 1).

The reflected optical signals 73, 75 shown in FIG. 4 have been shown at an exaggerated angle in order to show the optical signals clearly.

In some embodiments, the optical fiber 45 is a single fiber. In other embodiments, the optical fiber 45 may include: an optical fiber 45-1 configured to convey the first part 73 of the optical signal 71 from the beam-splitter-combiner 66 to the reflector 43; and an optical fiber 45-2 configured to convey the first part 73 of the optical signal 71 reflected by the reflector 43 to the beam splitter-combiner 66.

In some embodiments, optical fibers 72 may connect one or more of the following: the light source 68 with the beam splitter-combiner 66; the beam splitter-combiner 66 with the reflector 64; and/or the beam splitter-combiner 66 with the detector 70. In some embodiments, the beam splitter-combiner 66 may comprise a directional optical fiber coupler configured to couple with the optical fibers 45, 72 and perform the functions of the beam splitter-combiner 66 described above.

In some embodiments, the elements of the interferometer 37 may be distributed among the console 48 and the phacoemulsification probe 12 differently than described above. In other embodiments, all of the elements of the interferometer 37 may be disposed in the phacoemulsification probe 12.

Figure 5:
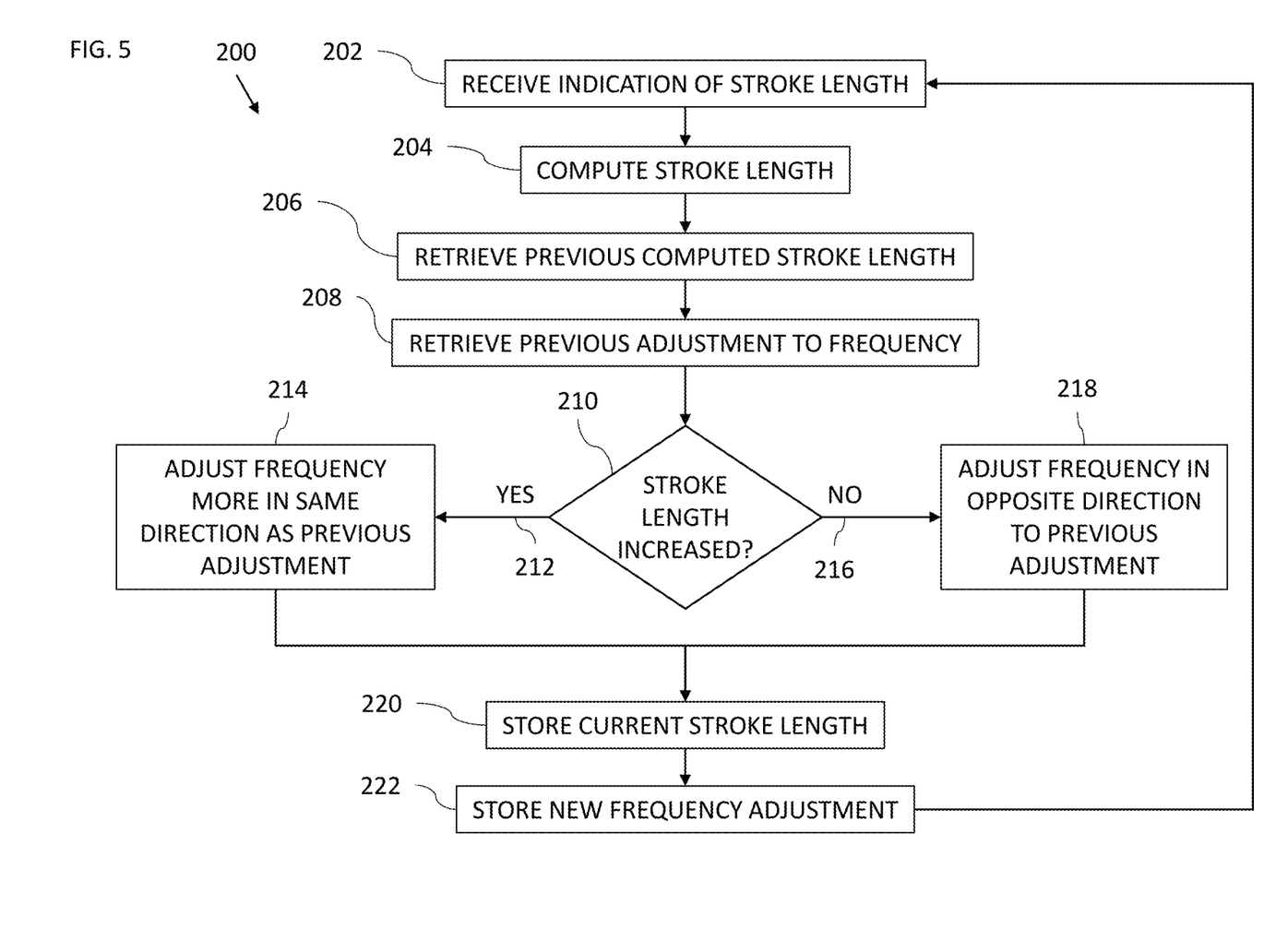
FIG. 5 is a flowchart including more detailed steps in part of the method of FIG. 2.

Reference is now made to FIG. 5, which is a flowchart 200 including more detailed steps in part of the method of FIG. 2. Reference is also made to FIG. 1.

The controller 38 (FIG. 1) is configured to receive an indication of stroke length from the detector 70 (FIG. 4) (block 202). In some embodiments, the controller 38 is configured to compute the stroke length (block 204) responsively to the received indication of stroke length. The computation of the stroke length may include converting the indication of stroke length from an analog form to a digital form. In some embodiments, the step of block 204 is not performed and the remainder of the steps below are performed using the indication of stroke length received from the detector 70, which may be received in a digital or analog form.

The controller 38 is configured to retrieve a previous computed stroke length (i.e., the stroke length computed prior to the newly computed stroke length) from a memory (not shown) (block 206) and to retrieve a previous adjustment to the drive frequency (i.e., computed based on the previous stroke length) (block 208).

The controller 38 is configured to compare the newly computed stroke length with the previous computed stroke length to determine whether the newly computed stroke length represents an increase over the previous computed stroke length in a step of decision block 210.

If the newly computed stroke length represents an increase over the previous computed stroke length (branch 212), the controller 38 is configured to adjust the drive frequency more in the same direction as the previous adjustment (block 214). For example, if the previous adjustment increased the drive frequency, the current adjustment will increase the drive frequency again, and vice-versa. If the newly computed stroke length represents a decrease over the previous computed stroke length (branch 216), the controller 38 is configured to adjust the drive frequency in the opposite direction to the previous adjustment (block 218). The adjustment to the frequency may be proportional to the computed stroke length or the adjustment may be a fixed value.

The controller 38 is configured to store the current computed stroke length (i.e., the newly computed stroke length) (block 220) and to store the new frequency adjustment (block 222).

The steps of the flowcharts 100 and 200 described herein may be performed in any suitable order with some of the steps optionally being performed simultaneously where possible.

Figure 6:
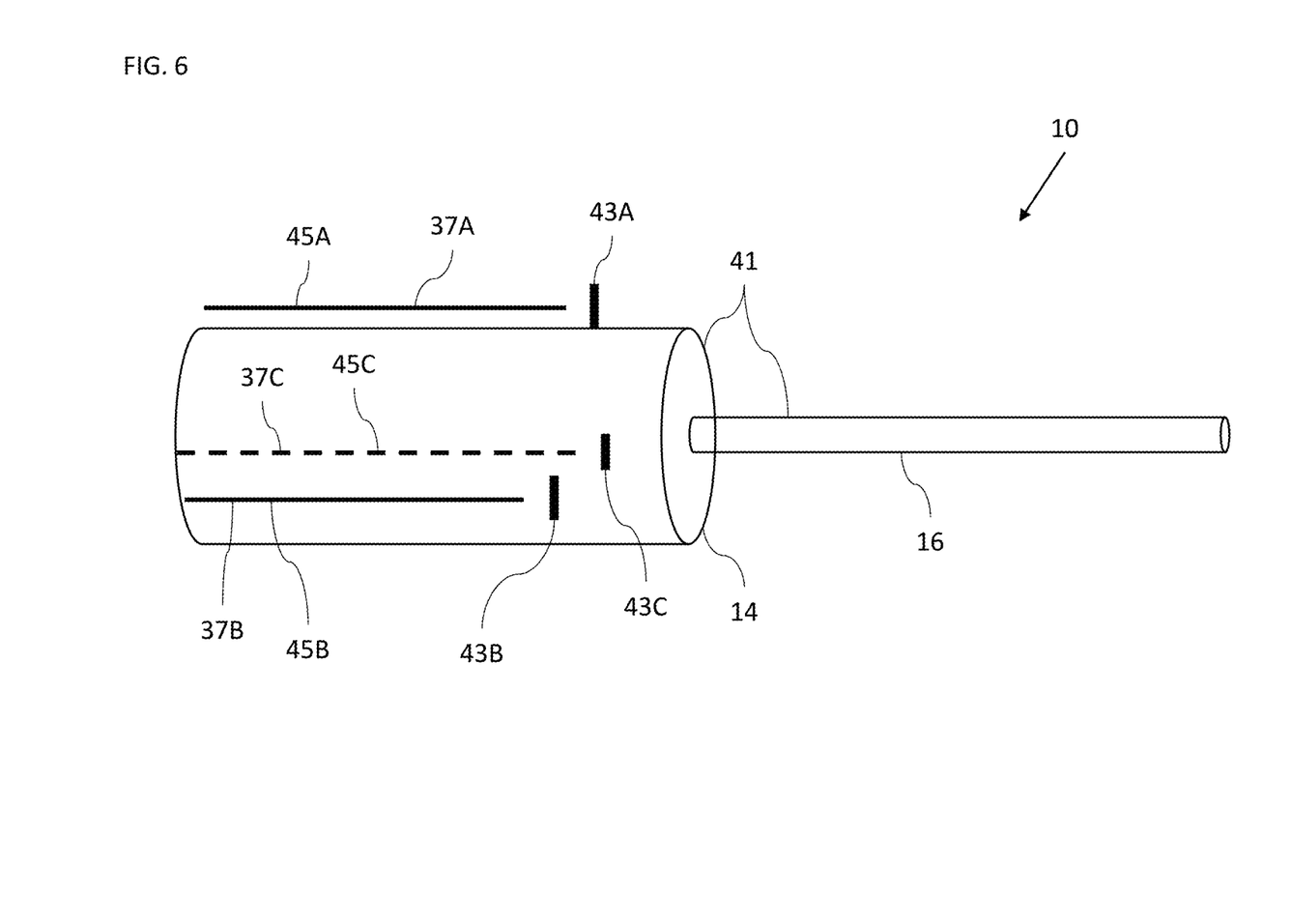
FIG. 6 is a schematic view of multiple interferometers for use in the system of FIG. 1.

Reference is now made to FIG. 6, which is a schematic view of multiple interferometers 37A, 37B, 37C for use in the system 10 of FIG. 1.

As previously mentioned, the vibrating portion 41 (including the horn 14 and needle 16) may vibrate in a vibration direction, which may include any one or more of the following: a longitudinal direction; a transverse direction; a torsional direction, or any suitable combination thereof. In order to measure the stroke length in any one or more of the vibration directions, the phacoemulsification system 10 may include multiple interferometers 37A, 37B, 37C. The distance measured by each of the interferometers 37A, 37B, 37C may be used by the controller 38 to compute the stroke length and optionally the direction of the stroke.

FIG. 6 shows three reflectors 43A, 43B, 43C disposed on the horn 14 and three respective optical fibers 45A, 45B, 45C of three respective interferometers 37A, 37B, 37C. It should be noted that each interferometer 37A, 37B, 37C also includes other components such as a light source, detector, beam splitter-combiner and another reflector. These additional components have not been shown for the sake of simplicity, but have been described above with respect to interferometer 37.

In FIG. 6, the reflectors 43A, 43B, 43C are disposed with an equal spacing around the horn 14. The reflector 43C, and the corresponding optical fiber 45C are disposed on the far side of the horn 14 and therefore optical fiber 45C is shown as a dotted line. However, in some embodiments the spacing may be unequal.

The distance between each reflector 43A, 43B, 43C and corresponding optical fiber 45A, 45B, 45C is measured by the corresponding interferometer 37A, 37B, 37C in substantially the same way as described above with reference to the interferometer 37 of FIGS. 1-5. If the distance measured by each interferometer 37A, 37B, 37C is the same, this indicates that the vibrating portion 41 is vibrating in a longitudinal direction. If the distance measured by each interferometer 37A, 37B, 37C is not the same, then this indicates that the vibrating portion 41 has another directional component, e.g. a transverse and/or torsional component. The indication of distance measured by each interferometer 37A, 37B, 37C is provided to the controller 38 which computes the stroke length and optionally the stroke direction and performs an algorithm (such as a gradient descent algorithm)

to maximize the stroke length. As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 72% to 108%.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and sub-combinations of the various features described hereinabove, as well as variations and modifications thereof which would occur to persons skilled in the art upon reading the foregoing description and which are not disclosed in the prior art.

What is claimed is:

1. A phacoemulsification method comprising:
   providing a phacoemulsification probe comprising a probe body, a vibrating portion, a stroke measurement device, and a piezoelectric actuator, wherein the vibrating portion comprises a needle and a horn, and wherein at least one part of the stroke measurement device is coupled with the probe body or the vibrating portion;
   inserting the needle into an eye;
   generating a drive signal to drive a vibration of the piezoelectric actuator which causes vibration of the needle in a direction having a stroke length with respect to the probe body of the phacoemulsification probe;
   providing indications of the stroke length of the needle over time; and
   dynamically adjusting a frequency of the drive signal so as to maximize the stroke length and maintain mechanical resonance of the needle responsively to the provided indications of the stroke length; wherein the stroke measurement device comprises an interferometer.

2. The method according to claim 1, wherein the direction comprises any one or more selected from the group consisting of a longitudinal direction, a transverse direction, and a torsional direction.

3. The method according to claim 1, wherein the interferometer comprises a first part and a second part, wherein the first part is coupled with the vibrating portion, and wherein the second part is coupled with the probe body.

4. The method according to claim 3, wherein the first part of the interferometer includes a first reflector and the second part of the interferometer includes at least one optical fiber coupled with the probe body.

5. The method according to claim 4, wherein the first reflector is coupled with the horn of the vibrating portion.

6. The method according to claim 4, further comprising:
   receiving an optical signal from a light source;
   splitting the received optical signal into a first part directed to the first reflector and a second part directed to a second reflector; and
   combining the first part reflected by the first reflector and the second part reflected by the second reflector into a combined optical signal.

7. The method according to claim 6, wherein the at least one optical fiber includes a first optical fiber and a second optical fiber.

8. The method according to claim 6, wherein the splitting and combining are performed by a directional optical fiber coupler.

9. The method according to claim 7, further comprising:
   conveying the first part of the optical signal from a beam-splitter-combiner to the first reflector in the first optical fiber; and
   conveying the first part of the optical signal reflected by the first reflector to the beam-splitter-combiner in the second optical fiber.

10. The method according to claim 1, wherein the stroke measurement device is configured to measure the stroke length of the needle over time.

11. The method according to claim 1, wherein the interferometer includes a Michelson Interferometer.

12. The method according to claim 4, wherein the interferometer further includes a third part, wherein the third part is coupled with a surgical console, and wherein the third part comprises at least one of a second reflector, a beam splitter-combiner, a light source configured to generate an optical signal, or a detector.

13. The method according to claim 4, wherein the interferometer includes a third part, wherein the third part is coupled with a surgical console, wherein the third part comprises at least a beam splitter-combiner, and wherein the at least one optical fiber extends from the probe body to the beam splitter-combiner in the surgical console.

* * * * *